United States Patent
Cifter et al.

(10) Patent No.: US 9,114,085 B2
(45) Date of Patent: *Aug. 25, 2015

(54) MODIFIED RELEASE PHARMACEUTICAL COMPOSITIONS OF DEXLANSOPRAZOLE

(71) Applicant: SANOVEL ILAC SANAYI VE TICARET ANONIM SIRKETI, Istanbul (TR)

(72) Inventors: Umit Cifter, Istanbul (TR); Ali Turkyilmaz, Istanbul (TR); Ibrahim Murat Uzer, Istanbul (TR); Alper Terkinli, Istanbul (TR); Levent Oner, Ankara (TR)

(73) Assignee: Sanovel Ilac Sanayi Ve Ticaret Anonim Sirketi, Istanbul (TR)

( * ) Notice: Subject to any disclaimer, the term of this patent is extended or adjusted under 35 U.S.C. 154(b) by 0 days.

This patent is subject to a terminal disclaimer.

(21) Appl. No.: 14/274,987

(22) Filed: May 12, 2014

(65) Prior Publication Data

US 2014/0255484 A1    Sep. 11, 2014

Related U.S. Application Data

(63) Continuation of application No. 13/101,220, filed on May 5, 2011, now Pat. No. 8,741,345.

(51) Int. Cl.
| | |
|---|---|
| *A61K 9/24* | (2006.01) |
| *A61K 9/20* | (2006.01) |
| *A61K 9/50* | (2006.01) |
| *A61K 31/4439* | (2006.01) |

(52) U.S. Cl.
CPC ............... *A61K 9/209* (2013.01); *A61K 9/2077* (2013.01); *A61K 9/2086* (2013.01); *A61K 9/2095* (2013.01); *A61K 9/5026* (2013.01); *A61K 9/5042* (2013.01); *A61K 9/5073* (2013.01); *A61K 31/4439* (2013.01)

(58) Field of Classification Search
None
See application file for complete search history.

(56) References Cited

U.S. PATENT DOCUMENTS

| | | |
|---|---|---|
| 2004/0247677 A1 | 12/2004 | Oury et al. |
| 2006/0165797 A1 | 7/2006 | Plachetka |
| 2008/0076766 A1 | 3/2008 | Herold et al. |
| 2009/0098199 A1 | 4/2009 | Lee et al. |
| 2009/0263475 A1 | 10/2009 | Manne et al. |

FOREIGN PATENT DOCUMENTS

| | | |
|---|---|---|
| EP | 0 629 398 A1 | 12/1994 |
| EP | 1 129 088 A2 | 9/2001 |
| EP | 1 930 030 A1 | 6/2008 |
| EP | 1 967 184 A1 | 9/2008 |
| WO | 2006/049565 A1 | 5/2006 |

OTHER PUBLICATIONS

Extended European Search Report dated Feb. 1, 2012 in European Patent Application No. 11164758.2.
Extended European Search Report dated Dec. 9, 2011 in European Patent Application No. 11164774.9.
Harianawala, A. et al., "Measurement of pH 1-10 near dissolving enteric coatings," International Journal of Pharmaceutics, vol. 247, 2002, pp. 139-146.
Metz et al., "Review Article: dual delayed release formulation of dsxlansoprazole MR, a novel approach to overcome the limitations of conventional single release proton pump inhibitor therapy," Alimentary Pharmacology & Therapeutics, Blackwell Scientific Publications Ltd., Cambridge, GB, vol. 29, No. 9, May 1, 2009, pp. 928-937.
Search Report and Written Opinion dated Mar. 1, 2011 in Turkish Patent Application No. TR201006225, filed Jul. 28, 2010.
Search Report and Written Opinion dated Mar. 2, 2011 in Turkish Patent Application No. TR201007007, filed Aug. 23, 2010.
Search Report and Written Opinion dated Apr. 26, 2012 in Turkish Patent Application No. TR201003557, filed May 5, 2010.

*Primary Examiner* — David J Blanchard
*Assistant Examiner* — Daniel F Coughlin
(74) *Attorney, Agent, or Firm* — Kenyon & Kenyon LLP

(57) ABSTRACT

Modified release oral pharmaceutical compositions of dexlansoprazole or pharmaceutically acceptable salts or hydrated forms thereof in the form of a bilayer tablet and processes for the manufacture of the tablet composition and its use in the treatment of gastrointestinal disorders.

17 Claims, No Drawings

MODIFIED RELEASE PHARMACEUTICAL COMPOSITIONS OF DEXLANSOPRAZOLE

CROSS REFERENCE TO RELATED APPLICATIONS

This application is a continuation of U.S. patent application Ser. No. 13/101,220, filed on May 5, 2011, which claims priority to Turkish Patent Application No. TR201003557, filed May 5, 2010, under relevant sections of 35 USC §119, the entire contents these applications are incorporated by reference therein.

FIELD OF THE INVENTION

The present invention is related to the modified release oral pharmaceutical compositions of dexlansoprazole or pharmaceutically acceptable salts or hydrated forms thereof in the form of a bilayer tablet and furthermore directed to processes for the manufacture of the tablet composition and its use in the treatment of gastrointestinal disorders.

BACKGROUND OF THE INVENTION

The active ingredient, dexlansoprazole is the R-enantiomer of lansoprazole which inhibits gastric acid secretion (a proton pump inhibitor). Its chemical name is (+)-2-[(R)-{[3-methyl-4-(2,2,2-trifluoroethoxy) pyridin-2-yl]methyl} sulfinyl]-1H-benzimidazole and its chemical structure is shown in the following Formula I.

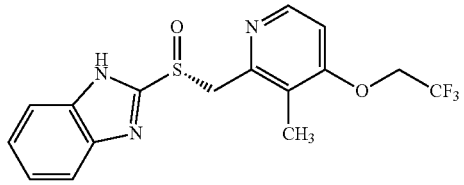

Formula I

A delayed release capsule form of dexlansoprazole is marketed and it is administered orally in a therapeutic dose of 30 mg and 60 mg.

As in the instance of other benzimidazole compounds, dexlansoprazole has also poor stability and is unstable to acidic medium, humidity, light and sensitive to heating. When orally administered, it may not be able to sufficiently activate, since it is decomposed by gastric acid and the like. Thus, several problems occur in formulating this compound into oral pharmaceutical dosage forms because of the acidic environment of the stomach. In particular, it will be rapidly decomposed and change color under moist conditions or in acidic to neutral aqueous solution.

When these compounds are formulated into pharmaceutical preparations for oral administration, they require special techniques to avoid contact of drug with gastric acid of the stomach. One technique most commonly used is to coat these compounds, or its granules or pellets, with an enteric coating. However, the material used in enteric coatings itself is acidic, which can cause the decomposition of the compound. Such decomposition occurs even during the enteric coating process, which results in the coloration of the surface of the drug-containing core.

Enteric films do not show high flexibility so that compression stress can yield rupturing of the film. It is therefore necessary to use a tableting technique that endorses the compression strain and maintains the acid resistance of the formulation after compression of the granules. Therefore caution is needed to be taken while compressing the tablets to form bilayer dosage form. Such a formulation has to be compressed in a specific hardness.

In the prior art, there are many patents including benzimidazoles such as lansoprazole and its R-enantiomer, dexlansoprazole in several different pharmaceutical compositions. Crystal form of R-lansoprazole is described in EP-B1-1129088.

EP-A1-0629398 describes a dosage form comprising a drug and an organic acid in a core surrounded by a film that controls the start of release, and further covered by an enteric coating layer. This dosage form is not suitable for substances that are sensitive to acidic degradation as the core comprises an organic acid.

Thus, there is still a need for developing pharmaceutical formulations of dexlansoprazole wherein good stability is achieved in a technologically simple way including an improved manufacturing process which overcomes the above described problems and provides a bioavailable pharmaceutical composition according to the formulations currently used.

The pharmaceutical formulation of this invention advantageously provides a bilayer tablet dosage form which is bioequivalent to a capsule dosage form of the same or substantially similar strength. The tablet dosage form can further be advantageous in that the manufacturing process can require fewer steps, e.g., eliminate the need for pellet formation and/or coating of those pellets, with no need for the additional expense of providing capsule shells.

Further advantages and embodiments of the present invention will become apparent from the following description.

SUMMARY AND DESCRIPTION OF THE INVENTION

The main object of the present invention is to provide a stable modified release oral pharmaceutical composition of dexlansoprazole or pharmaceutically acceptable salts or hydrated forms thereof in the form of a bilayer tablet previously undisclosed in the prior art, wherein the compression force to form the bilayer tablet is between 2 to 30 kN.

Another object of the present invention is to express a pharmacological effect of the active ingredient stably and rapidly after administration and sustain a pharmalogical effect of the dual release for a prolonged period of time and therefore to have a desired release profile.

Yet another object of the present invention is to provide an improved and simple process for preparing the modified release oral pharmaceutical composition of dexlansoprazole or pharmaceutically acceptable salts or hydrated forms thereof in the form of a bilayer tablet.

As used herein, "rate controlling agent" means an excipient in the first layer of the final dosage form whose primary function is to modify the duration of release of the active drug substance from the dosage form.

In this invention, we had a desired dual release profile of the modified release oral pharmaceutical compositions of dexlansoprazole or pharmaceutically acceptable salts or hydrated forms thereof in the form of a bilayer tablet by using the controlled release agents independently from the coating, in other words the controlled release agents are not placed in the coating. Surprisingly, this is achieved by adding these controlled release agents only to the first layer of the bilayer tablet, not in to the whole bilayer tablet. This also prevents the dose dumping of the active ingredient, which can be a serious problem caused by the wrong design of the modified release formulations.

Dose dumping is one of the most important disadvantages of modified release dosage forms. It is difficult to develop modified release formulations of benzimidazoles for several different reasons, although there are many modified release formulations formulated with different coatings. First of all, modified release formulations of these medicaments can be prone to "dose dumping" in which the release of the active ingredient is delayed but once the release begins the medicament may be released very fast. The most critical factor of dose dumping is the amount of the active substance released early on. Therefore, the active ingredient concentration in the plasma will increase suddenly and this may lead to toxicity.

Another object of this present invention is to have a desired release profile and an improved stability to maximize the mechanical resistance of the bilayer tablets. This modified release oral pharmaceutical bilayer tablet formulation has been designed by using one type of enteric coating which dissolves under pH 5.5 or above and coated granules are compressed in a specific hardness to form the bilayer tablets. Enteric films do not show high flexibility so that compression stress can yield rupturing of the film. Therefore, caution is needed to be taken while compressing the tablets to form bilayer dosage form. Thus, the bilayer tablets of this present invention are compressed to a hardness of between 2 to 30 kN, and preferably between 3 to 12 kN.

According to another object of the present invention, these bilayer tablets are again coated with the same enteric coating dispersion so as to prevent any problems which may occur during the tablet's shelf-life.

According to the main object of the present invention, a modified release oral pharmaceutical composition of dexlansoprazole or pharmaceutically acceptable salts or hydrated forms thereof in the form of a bilayer tablet is characterised in that a first layer comprises:
  i) a film-coated core comprising dexlansoprazole or pharmaceutically acceptable salts or hydrated forms thereof with one or more pharmaceutically acceptable excipient;
    ii) an enteric coating that dissolves at pH 5.5 or higher; and
    iii) a rate controlling agent that dissolves independently from pH;
and the bilayer tablet having a film-coated second layer comprising dexlansoprazole or pharmaceutically acceptable salts or hydrated forms thereof with one or more pharmaceutically acceptable excipient, wherein the compression force to form the bilayer tablet is between 2 to 30 kN.

In one embodiment, the enteric coating in the first layer of the bilayer tablet (ii) that dissolves at pH 5.5 or higher is selected from the group consisting of cellulose acetate phthalate, cellulose acetate succinate, hydroxpropyl cellulose phthalate, hydroxpropyl ethylcellulose phthalate, hydroxyl propyl methyl cellulose phthalate, hydroxyl propyl methyl cellulose acetate succinate, hydroxyethyl cellulose phthalate, methylcellulose phthalate, polyvinyl acetate phthalate, polyvinylacetate hydrogen phthalate, amylase acetate phthalate, cellulose ester phthalates, cellulose ether phthalates, sodium cellulose acetate phthalate, starch acid phthalate, cellulose acetate butyrate, cellulose acetate maleate, cellulose acetate trimellitate, cellulose acetate propionate, styrene maleic acid dibutyl phthalate copolymer, styrene maleic acid polyvinyl acetate phthalate copolymer propionate, shellac or mixtures thereof.

In another embodiment, the rate controlling agent in the first layer of the bilayer tablet (iii) that does dissolves independently from pH is selected from the group consisting of ethyl cellulose, methyl cellulose, hydroxypropyl cellulose, low-substituted hydroxylpropyl cellulose, hydroxypropyl methyl cellulose, hydroxymethyl cellulose, hydroxylethyl cellulose, hydroxypropyl ethyl cellulose, carboxyethyl cellulose, carboxymethyl hydroxyethyl cellulose, carbomer, sodium carboxymethyl cellulose, polyvinylpyrrolidone, polyethylene oxide, glyceryl behenate, glyceryl palmitate, glyceryl oleate, glyceryl stearate, glcyeryl palmitostearate, sodium alginate, calcium alginate, potassium alginate, propylene glycol alginate, complex salt of alginic acids, vinyl acetate/crotonic acid copolymers, maleic anhydride/methyl vinyl ether copolymers, stearic acid, stearyl alcohol, cetyl alcohol, palmityl alcohol, waxes, zein, chitosan, or mixtures thereof.

Yet another embodiment of the invention is to have a film coating between the core and the enteric coating of the first layer and/or may be under the enteric coating of the bilayer tablet. The film coating layer is selected from the group consisting of polyvinyl alcohol, polyvinylpyrrolidone (PVP), hydroxypropyl cellulose, low-substituted hydroxypropyl cellulose, hydroxypropylmethyl cellulose, sodium carboxymethyl cellulose, methyl and ethyl cellulose, hydroxyethyl methylcellulose, polyethylen glycol (PEG), PVP/vinyl acetate copolymer, PVA/PEG copolymer, alginates, sugar, starch, sugar alcohols (such as D-mannitol, erythritol, etc)or mixtures thereof.

According to one embodiment, the amount of dexlansoprazole or pharmaceutically acceptable salts or hydrated forms thereof is from 5% to 50% by weight of the total tablet.

Surprisingly it is found that, when the weight ratio of the polymers in enteric coating (ii) to rate controlling agents (iii) in first layer of the bilayer tablet is 10:1 to 1:10, a synergistic effect is obtained over the release rate of the dexlansoprazole.

In one embodiment, the amount of polymers in enteric coating are from 0.5% to 30% by weight of the bilayer tablet and the amount of rate controlling agents are from 0.25% to 15% by weight of the bilayer tablet in the first layer of the bilayer tablet.

According to another object of the present invention, the modified release oral pharmaceutical composition of dexlansoprazole or pharmaceutically acceptable salts or hydrated forms thereof in the form of a bilayer tablet further comprises a film coating.

Yet another object of the present invention is to further comprise an enteric coating in an amount of 1% to 20% (w/w) of the total weight of the bilayer tablet, preferably in an amount of 2% to 10% (w/w), wherein the enteric coating dissolves at pH 5.5 or higher.

In one embodiment of the present invention, the bilayer tablet may comprise optionally a barrier layer between the two layers wherein the barrier layer is selected from the group consisting of corn starch, lactose, honey, sugar alcohol (D-mannitol, erythritol, etc.), low-substituted hydroxypropyl cellulose, hydroxypropyl cellulose, hydroxypropyl methylcellulose, polyvinylpyrrolidone, polyvinyl alcohol, methylcellulose, hydroxyethyl methylcellulose or mixtures thereof.

The modified release pharmaceutical composition of this invention comprise one or more pharmaceutically acceptable excipients selected from the group comprising binders, diluents, fillers, lubricants, glidants, disintegrants, basic stabilizers, coloring agents or flavoring agents.

Suitable binders may comprise but are not limited to methyl cellulose, ethyl cellulose, hydroxypropyl methyl cellulose, hydroxypropyl cellulose, sodium carboxymethyl cellulose, polyvinyl pyrrolidone, polyvinyl alcohol, polymethacrylates, starch, gelatin, alginic acid, sucrose and the like and mixtures thereof.

Suitable diluents and fillers may comprise but are not limited to microcrystalline cellulose, cellulose, lactose, starch, calcium phosphates, calcium sulphates, mannitol, glucose, sucrose, sorbitol and the like and mixtures thereof.

Suitable lubricants may comprise but are not limited to stearic acid, magnesium, calcium or sodium stearate, sodium stearyl fumarate, talc, waxes, liquid paraffin, and the like and mixtures thereof.

Suitable glidants may comprise but are not limited to talc, aluminium silicate, colloidal silica, starch and the like and mixtures thereof.

Suitable disintegrants may comprise but are not limited to alginic acid and salts, sodium carboxymethyl cellulose, hydroxypropyl methyl cellulose, starch, sodium starch glycolate, crosslinked polyvinyl pyrrolidone and the like and mixtures thereof.

The extended release pharmaceutical compositions of this invention are administrated orally and in the form of a once-a-day or twice-a-day dosage regimen.

In one embodiment, the dual release of the modified release oral pharmaceutical composition of dexlansoprazole or pharmaceutically acceptable salts or hydrated forms thereof in the form of a bilayer of this invention tablet is obtained by the invitro dissolution profiles tested.

In this present invention, surprisingly the problem is also solved by more efficient process to prepare a modified release oral pharmaceutical composition of dexlansoprazole or pharmaceutically acceptable salts or hydrated forms thereof in the form of a bilayer tablet comprising the following steps:

a) dexlansoprazole is dry mixed with the one or more pharmaceutically acceptable excipient in a powder blender;

b) blended powder is then granulated using water or alcohol;

c) wet granules are sieved and dried in an oven, when its moisture content is adequate it is then sieved again and covered with a film coating;

d) coated granules divided into two parts;

e) one part is then coated with an enteric coating, then rate controlling agents are added to these enteric coated granules;

f) the second part remains uncoated;

g) bilayer tablet compression is performed using these granules; and h) after the tablets are compressed with adequate hardness, they are coated again with an enteric coating in the outermost layer; optionally a film coating may be applied before enteric coating.

The modified release oral pharmaceutical composition of dexlansoprazole or pharmaceutically acceptable salts or hydrated forms thereof in the form of a bilayer tablet is used for the treatment of gastrointestinal disorders.

As apparent from the example below, by the method of the present invention the hardness of the bilayer tablet is improved. In addition, dissolution and stability is also improved.

This invention is further defined by reference to the following example. Although the example is not intended to limit the scope of the present invention, it should be considered in the light of the description detailed above. It will be apparent to those skilled in the art that many modifications, both to materials and methods, may be practiced without departing from the scope of the invention.

EXAMPLE 1

Dexlansoprazole and suitable excipients are blended together in a dry powder blender for about 20 minutes. The powder is then granulated using water in a shear mixer for about 15 minutes. Obtained granules are wet sieved through a 1.0 mm sieve and dried. The granules are then dry-sieved using a 0.5 mm sieve and covered with a film coating which comprises polyvinyl alcohol or hydroxypropylmethyl cellulose and the like or mixtures thereof, up to a weight gain of about 6% of the uncoated tablet core weight. Dispersion is obtained using a propeller stirrer and stirring at moderate speeds for approximately 45 minutes. Then these coated granules are divided into two parts as being about 60 to 85% to be covered with enteric coating and about 15 to 40% left uncoated before the tablet compression process.

Then, enteric coating agents are added slowly under moderate mixing speeds and stirred for about 30 minutes. Afterwards water and lubricants and/or glidants are added and the mixture is stirred for an additional 10 minutes before being used in the coating process. Approximately 60 to 85% portion of the granules are coated with this enteric coating dispersion. Rate controlling agents are then added to these enteric coated granules.

The granules are then dried again, sieved through a 0.5 mm sieve, lubricant/s added to the granules and mixed for an additional 5 minutes. The enteric coated granules are then taken to the tablet compression stage, together with the film coated granules to form bilayer tablets.

Bilayer tablets are compressed in a hardness of between 2 to 30 kN, preferably between 3 to 12 kN, more preferably between 4 to 10 kN. These tablets are then coated in a pan coater with the aforementioned enteric coating and optionally with non-enteric coating.

The invention claimed is:

1. A bilayer tablet for modified release comprising
   (a) a first layer comprising
      (I) granules, wherein individual granules comprise a core comprising dexlansoprazole or pharmaceutically acceptable salts or hydrated forms thereof and one or more pharmaceutically acceptable excipients, wherein the core is coated with a film, and wherein the film-coated core is coated with an enteric coating that dissolves at pH 5.5 or higher, wherein the enteric coating in the first layer comprises at least one substance selected from cellulose acetate phthalate, cellulose acetate succinate, hydroxpropyl cellulose phthalate, hydroxypropyl ethylcellulose phthalate, hydroxyl propyl methyl cellulose phthalate, hydroxyl propyl methyl cellulose acetate succinate, hydroxyethyl cellulose phthalate, methylcellulose phthalate, polyvinyl acetate phthalate, polyvinylacetate hydrogen phthalate, amylase acetate phthalate, cellulose ester phthalates, cellulose ether phthalates, sodium cellulose acetate phthalate, starch acid phthalate, cellulose acetate butyrate, cellulose acetate maleate, cellulose acetate trimellitate, cellulose acetate propionate, styrene maleic acid dibutyl phthalate copolymer, styrene maleic acid polyvinyl acetate phthalate copolymer propionate, shellac, and mixtures thereof; and
      (II) a rate controlling agent that dissolves independently from pH; and
   (b) a second layer comprising film-coated granules comprising dexlansoprazole or pharmaceutically acceptable salts or hydrated forms thereof and one or more pharmaceutically acceptable excipients;
      wherein the rate controlling agent is in only the first layer and not in the second layer or an optional enteric coating of the entire tablet, wherein a weight ratio of the at least one substance in the enteric coating in the first layer to the rate controlling agent in the first layer is 10:1 to 1:10, and
wherein the bilayer tablet is formed with a compression force between 2 to 30 kN.

2. The bilayer tablet of claim 1, wherein the rate controlling agent in the first layer is selected from ethyl cellulose, methyl cellulose, hydroxypropyl cellulose, low-substituted hydroxylpropyl cellulose, hydroxypropyl methyl cellulose, hydroxymethyl cellulose, hydroxyethyl cellulose, hydroxypropyl ethyl cellulose, carboxyethyl cellulose, carboxymethyl hydroxyethyl cellulose, carbomer, sodium carboxymethyl cellulose, polyvinylpyrrolidone, polyethylene oxide, glyceryl behenate, glyceryl palmitate, glyceryl oleate, glyceryl stearate, glyceryl palmitostearate, sodium alginate, calcium alginate, potassium alginate, propylene glycol alginate, complex salt of alginic acids, vinyl acetate/crotonic acid copolymers, maleic anhydride/methyl vinyl ether copolymers, stearic acid, stearyl alcohol, cetyl alcohol, palmityl alcohol, waxes, zein, chitosan, and mixtures thereof.

3. The bilayer tablet of claim 1, wherein the film coating the core in the first layer comprises a substance selected from polyvinyl alcohol, polyvinylpyrrolidone (PVP), hydroxypropyl cellulose, low-substituted hydroxypropyl cellulose, hydroxypropylmethyl cellulose, sodium carboxymethyl cellulose, methyl and ethyl cellulose, hydroxyethyl methylcellulose, polyethylene glycol (PEG), PVP/vinyl acetate copolymer, PVA/PEG copolymer, alginates, sugar, starch, sugar alcohols, and mixtures thereof.

4. The bilayer tablet of claim 1, wherein the film of the film-coated granules in the second layer comprises a substance selected from polyvinyl alcohol (PVA), polyvinylpyrrolidone (PVP), hydroxypropyl cellulose, low-substituted hydroxypropyl cellulose, hydroxypropylmethyl cellulose, sodium carboxymethyl cellulose, methyl and ethyl cellulose, hydroxyethyl methylcellulose, polyethylene glycol (PEG), PVP/vinyl acetate copolymer, PVA/PEG copolymer, alginates, sugar, starch, sugar alcohols, and mixtures thereof.

5. The bilayer tablet of claim 1, wherein the second layer is not enteric coated.

6. The bilayer tablet of claim 1, further comprising an enteric coating on the bilayer tablet.

7. The bilayer tablet of claim 6, further comprising a film under the enteric coating of the bilayer tablet.

8. The bilayer tablet of claim 1, further comprising a non-enteric coating on the bilayer tablet.

9. The bilayer tablet of claim 1, further comprising a film coating.

10. The bilayer tablet of claim 1, further comprising a barrier layer between the first layer and second layer, wherein the barrier layer comprises a substance selected from corn starch, lactose, honey, sugar alcohol, low-substituted hydroxypropyl cellulose, hydroxypropyl cellulose, hydroxypropyl methylcellulose, polyvinylpyrrolidone, polyvinyl alcohol, methylcellulose, hydroxyethyl methylcellulose, and mixtures thereof.

11. The bilayer tablet of claim 1, wherein the one or more pharmaceutically acceptable excipients are selected from binders, diluents, fillers, lubricants, glidants, disintegrants, basic stabilizers, coloring agents, and flavoring agents.

12. The bilayer tablet of claim 11, wherein the binders comprise methyl cellulose, ethyl cellulose, hydroxypropyl methyl cellulose, hydroxypropyl cellulose, sodium carboxymethyl cellulose, polyvinyl pyrrolidone, polyvinyl alcohol, polymethacrylates, starch, gelatin, alginic acid, sucrose, or mixtures thereof.

13. The bilayer tablet of claim 11, wherein the diluents or fillers comprise microcrystalline cellulose, cellulose, lactose, starch, calcium phosphates, calcium sulphates, mannitol, glucose, sucrose, sorbitol, or mixtures thereof.

14. The bilayer tablet of claim 11, wherein the lubricants comprise stearic acid, magnesium, calcium or sodium stearate, sodium stearyl fumarate, talc, waxes, liquid paraffin, or mixtures thereof.

15. The bilayer tablet of claim 11, wherein the glidants comprise talc, aluminium silicate, colloidal silica, starch, or mixtures thereof.

16. The bilayer tablet of claim 11, wherein the disintegrants comprise alginic acid and salts, sodium carboxymethyl cellulose, hydroxypropyl methyl cellulose, starch, sodium starch glycolate, crosslinked polyvinyl pyrrolidone, and mixtures thereof.

17. The bilayer tablet of claim 1 having a dual release profile of dexlansoprazole after oral administration.

* * * * *